US00PP09774P

United States Patent [19]

Utecht

[11] Patent Number: Plant 9,774

[45] Date of Patent: Dec. 31, 1996

[54] GERANIUM PLANT NAMED 'FISBOOGY'

[75] Inventor: Angelika Utecht, Montabaur, Germany

[73] Assignee: Florfis AG, Binningen, Switzerland

[21] Appl. No.: 520,715

[22] Filed: Aug. 29, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium named Fisboogy, as described and illustrated, and particularly characterized by the combined features of orange-red semi-double flowers in large umbels, dark green, well zoned foliage, medium, well branched plant habit and comparatively early flower response.

1 Drawing Sheet

The present invention comprises a new and distinct cultivar of geranium, botanically known as *Pelargonium zonale,* and hereinafter referred to by the cultivar name Fisboogy.

Fisboogy is a product of a planned breeding program which had the objective of creating new geranium cultivars with orange-red to red flower color in combination with dark green foliage and well branched plant habit.

Fisboogy was originated form a hybridization made by the inventor Angelika Utecht in a controlled breeding program in Hillscheid, Germany, in 1991. The female parent was an unnamed hybrid seedling identified by the number K 88/731/2), and characterized by red single flowers, foliage with strong zonation, and vigorous growth. It was obtained by crossing the commercial varieties Vesuv and Bundeskanzler and then using one of the resulting seedlings as the female parent in a cross wih the cultivar Fiswig, disclosed in U.S. Pat. No. P.P. 7,385. Vesuv is an early flowering, red colored variety with medium green foliage and weak zonation. Bundeskanzler has single orange-red flowers and medium green foliage, while Fiswig is characterized by single carmine flowers and dark green foliage.

The male parent of Fisboogy was also an unnamed hybrid seedling (No. K 88/1084/1) having orange-red semi-double flowers and dark green foliage with strong zonation. It was derived from crossings between the commercial cultivars Springtime Irene, a tetraploid line of Stadt Bern, and Kops. Springtime Irene is characterized by salmon pink flower color, medium green zoned foliage and vigorous growth habit. Stadt Bern has single orange-red flowers and dark green foliage with strong zonation, while Kops has single red flowers in combination with medium green, weakly zoned foliage.

Fisboogy was discovered and selected as one flowering plant within the progeny of the stated cross by Angelika Utecht in Spring 1992 in a controlled environment in Galdar, Gran Canaria, Spain.

The first act of asexual reproduction of Fisboogy was accomplished when vegetative cuttings were taken from the initial selection in June 1992 in a controlled environment in Galdar, Gran Canaria, Spain, by, or under the supervision of, the inventor.

Horticultural examination of plants grown from these cuttings initiated in May, 1993 in Hillscheid, Federal Republic of Germany, and continuing thereafter, has demonstrated that the combination of characteristics as herein disclosed for Fisboogy are firmly fixed and are retained through successive generations of asexual reproduction.

Fisboogy has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisboogy, which in combination distinguish this geranium as a new and distinct cultivar:

1. Intense orange-red flower color.
2. Flowers of semi-double form and medium size.
3. Large broad umbels.
4. Dark green foliage with distinct zonation.
5. Medium plant habit.
6. Comparatively early flower response.

Of the many commercial cultivars known to the present inventor, the most similar in comparison to Fisboogy are the cultivars Fisdia and Tango, disclosed in U.S. Pat. Nos. P.P. 8,727 and 5,933, respectively. Reference is made to attached Chart A.

In general comparison to Fisdia and Tango, Fisboogy has zoned foliage, shorter peduncles which produce a more compact plant, and better heat tolerance.

The accompanying photographic drawing is a top perspective view which shows typical flower and foliage characteristics of Fisboogy, with colors being as true as possible with illustrations of this type.

In the following description, color references are made to The Royal Horticultural Society Colour Chart. The color values were determined indoors from flowers taken from plants grown in a greenhouse in May 1994 in Hilscheid, Federal Republic of Germany.

Classification:

*Botanical.*—A hybrid of the species *Pelargonium zonale l'Hert.*

*Commercial.*—Zonal geranium, cv., Fisboogy.

INFLORESCENCE

Umbel:

*Shape.*—Flat semi-spherical to umbrella-shaped.

*Average diameter.*—125 mm.

*Average depth.*—55 mm.

*Peduncle length.*—115 mm.

*Peduncle color.*—Green, upper end red.

*Pedicel length.*—26 mm.

*Pedicel color.*—Light to dark red.

*Number of flowers per umbel.*—26.

Corolla:

*Average diameter.*—45 mm.

*Form.*—Semi-double.
*Number of petals.*—9–11.
*Number of petaloids.*—2–3.
*Color (general tonality from a distance of three meters).*—Orange-red.
*Color of upper petals.*—43 A.
*Markings of upper petals.*—No markings.
*Color of lower petals.*—43 A.
*Color of lower surface of petals.*—43 A-B.
*Color of sepals.*—Green, dark red at the base.
*Number of sepals.*—5.

Bud:
*Shape.*—Nearly round.
*Color (adaxial).*—Green, dark red at the base.
*Color (abaxial).*—Orange-red.

Reproductive organs:
*Androecium.*—3 Fertile anthers; white filaments, orange pollen.
*Gynoecium.*—5–6 l lobed stigma, red style and stigma.
*Seed.*—No seed set observed.

Spring flowering response period: In Hillscheid, Federal Republic of Germany, in 1994 plants of Fisboogy had on average 0.8 umbels with at least one flower opened 11 weeks after planting of unrooted cuttings.

Outdoor flower production: The flower count in 1994 in Hillscheid, Federal Republic of Germany indicated about 30 umbels per plant for May through August observation period.

Durability: Good shatter resistance.

PLANT

Foliage:
*Form.*—Kidney-shaped.
*Margin.*—Bicrenated.
*Size of leaf.*—90 mm.
*Color of upper surface.*—Dark green, approximately 137 A-147 A.
*Color of zonation.*—Brown, about 166 A.
*Tolerance of botrytis.*—Average.

General appearance and form:
*Internode length.*—20 mm.
*Branching pattern.*—1.5 branches per week.
*Height of foliage.*—28 cm (in June, 16-week old plants).

Ploidy: Tetraploid.

CHART A

| | FISBOOGY | FISDIA | TANGO |
|---|---|---|---|
| Flower color (RHS) | 43 A | 43 A | 44A–45B |
| Peduncle Length | 12 cm | 17 cm | 16 cm |
| Zonation | medium | very weak | very weak |
| Beginning of flowering (number of flowers 11 weeks after propagation | 0.8 | 0.8 | 0.5 |

I claim:

1. A new distinct cultivar of geranium plant named Fisboogy, as illustrated and described.

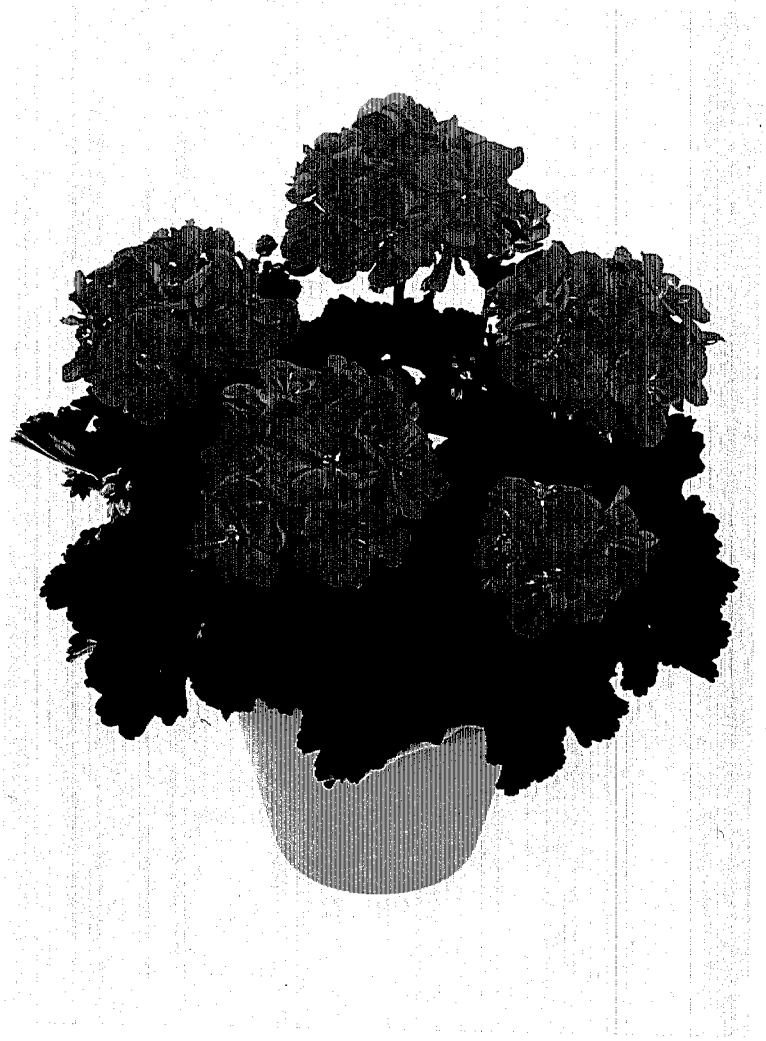

* * * * *